United States Patent
Lafont et al.

(10) Patent No.: US 12,351,823 B2
(45) Date of Patent: *Jul. 8, 2025

(54) MAMMALIAN CELL POPULATION AND MEDICAMENTS FOR CELL THERAPIES IN EQUINES AND IMPROVED CELL CULTIVATION METHODS

(71) Applicant: SCARCELL Therapeutics, Paris (FR)

(72) Inventors: Antoine Lafont, Paris (FR); Mathieu Castela, Clamart (FR)

(73) Assignee: Scarcell Technologies, Paris (FR)

( * ) Notice: Subject to any disclaimer, the term of this patent is extended or adjusted under 35 U.S.C. 154(b) by 14 days.

This patent is subject to a terminal disclaimer.

(21) Appl. No.: 18/301,856

(22) Filed: Apr. 17, 2023

(65) Prior Publication Data

US 2024/0307454 A1  Sep. 19, 2024

Related U.S. Application Data

(60) Provisional application No. 63/490,489, filed on Mar. 15, 2023.

(30) Foreign Application Priority Data

Mar. 15, 2023 (EP) ..................................... 23305350

(51) Int. Cl.
| | | |
|---|---|---|
| A61K 35/33 | (2015.01) | |
| A61K 9/08 | (2006.01) | |
| A61K 35/28 | (2015.01) | |
| A61K 35/38 | (2015.01) | |
| A61K 45/06 | (2006.01) | |
| A61P 19/00 | (2006.01) | |
| C12N 5/071 | (2010.01) | |
| C12N 5/077 | (2010.01) | |

(52) U.S. Cl.
CPC .............. *C12N 5/0632* (2013.01); *A61K 9/08* (2013.01); *A61K 35/28* (2013.01); *A61K 35/33* (2013.01); *A61K 35/38* (2013.01); *A61K 45/06* (2013.01); *A61P 19/00* (2018.01); *C12N 5/0656* (2013.01); *C12N 5/0692* (2013.01); *C12N 2500/32* (2013.01); *C12N 2500/84* (2013.01); *C12N 2501/115* (2013.01); *C12N 2501/2301* (2013.01); *C12N 2509/00* (2013.01)

(58) Field of Classification Search
CPC ..................................................... A61K 35/33
See application file for complete search history.

(56) References Cited

U.S. PATENT DOCUMENTS

| | | | |
|---|---|---|---|
| 7,951,593 | B2 | 5/2011 | Gogly et al. |
| 8,303,948 | B2 | 11/2012 | Gogly et al. |
| 8,609,085 | B2 | 12/2013 | Lafont et al. |
| 10,300,279 | B2 | 5/2019 | Fraga et al. |
| 10,624,838 | B2 | 4/2020 | Lafont et al. |
| 11,229,670 | B2 | 1/2022 | Lafont et al. |
| 2011/0097421 | A1 | 4/2011 | Gogly et al. |
| 2016/0008342 | A1* | 1/2016 | Chiamvimonvat .. A61K 31/336 424/93.7 |
| 2016/0151274 | A1 | 6/2016 | Lafont et al. |
| 2016/0256496 | A1 | 9/2016 | Gogly et al. |
| 2018/0028571 | A1 | 2/2018 | Gogly et al. |
| 2020/0268805 | A1 | 8/2020 | Lafont et al. |
| 2020/0306174 | A1 | 10/2020 | Lafont et al. |
| 2021/0156778 | A1 | 5/2021 | Gadea Ramos et al. |
| 2021/0238542 | A1 | 8/2021 | Kitano et al. |

FOREIGN PATENT DOCUMENTS

WO  WO-2023007244 A1  2/2023

OTHER PUBLICATIONS

Palkowitz et al., "Biofunctionalization of Dental Abutment Surfaces by Crosslinked ECM Proteins Strongly Enhances Adhesion and Proliferation of Gingival Fibroblasts", Advanced. Healthcare Materials, 2021, 10(10), pp. 1-12. (Year: 2021).*
Fournier et al., "Multipotent Progenitor Cells in Gingival Connective Tissue", Tissue Engineering: Part A, 2010, vol. 16, No. 9, pp. 2891-2899. (Year: 2010).*
Magne et al "IL-1β-Primed Mesenchymal Stromal Cells Improve Epidermal Substitute Engraftment and Wound Healing via Matrix Metalloproteinases and Transforming Growth Factor-β1", Journal of Investigative Dermatology, 2020, vol. 140, pp. 688-698. (Year: 2020).*
Medical Dictionary, definition for heterogeneous, https://medical-dictionary.thefreedictionary.com/heterogeneous, 2012, p. 1 (Year: 2012).*
Diar-Bakirly et al., Human gingival fibroblasts: Insolation, characterization, and evaluation of CD146 expression, Saudi Journal of Biological Sciences, 28:2518-2526 (Jan. 2021).
Ahangar et al. "Human gingival fibroblast secretome accelerates wound healing through anti-inflammatory and pro-angiogenic mechanisms," Regenerative Medicine, 5(24): 1-10 (2020).
Brown et al., "Ability of the Canine Brief Pain Inventory to detect response to treatment in dogs with osteoarthritis," J Am Vet Med Assoc., 233(8):1278-1283 (Oct. 2008).
Ferre et al. "Formation of Cartilage and Synovial Tissue by Human Gingival Stem Cells," Stem Cells and Development, 23(23): 2895-2907 (Jul. 2014).

(Continued)

*Primary Examiner* — Laura Schuberg
(74) *Attorney, Agent, or Firm* — Eversheds Sutherland (US) LLP; Nicola A. Pisano

(57) ABSTRACT

Compositions of matter, including cell populations and medicaments, are provided that are derived from equine gingival fibroblasts and have cell phenotypes that occur in proportions not found in natural gum tissue, but rather, are preferentially are selected to express proteins favoring angiogenesis and anti-inflammatory effects, while reducing cell populations that promote tumorigenicity and/or formation of metalloproteinases that inhibit tissue regeneration. Methods of generating such compositions are provided that increase proliferation many-fold compared to previously known methods, and methods of using such compositions in a wide range of equine cell therapies are provided.

17 Claims, 8 Drawing Sheets
(3 of 8 Drawing Sheet(s) Filed in Color)

(56) References Cited

OTHER PUBLICATIONS

Grindberg et al., "RNA-sequencing from single nuclei," PNAS, 110(49):19802-19807 (Dec. 2013).
Hou et al., "Autologous Transplantation of Gingival Fibroblast-Like Cells and a Hydroxylapatite Complex Graft in the Treatment of Periodontal Osseous Defects: Cell Cultivation and Long-Term Report of Cases," Cell Transplantation, 12:787-797 (May 2003).
Linard et al., "Therapeutic Potential of Gingival Fibroblasts for Cutaneous Radiation Syndrome: Comparison to Bone Marrow-Mesenchymal Stem Cell Grafts," Stem Cells and Development, 24(10):1182-1193 (Jan. 2015).
Forough, et al., Overexpression of Tissue Inhibitor of Matrix Metalloproteinase-1 Inhibits Vascular Smooth Muscle Cell Functions In Vitro and In Vivo, Circulation Research, 79:812-820 (1996).
Guo et al., "Tissue inhibitors of metalloproteinases-1 (TIMP-1) and -2(TIMP-2) are major serum factors that stimulate the TIMP-1 gene in human gingival fibroblasts," Biochimica et Biophysica Acta, vol. 1763(3):296-304 (Feb. 2006).
Mao, et al., Gingiva-Derived Mesenchymal Stem Cell-Extracellular Vesicles Activate Schwann Cell Repair Phenotype and Promote Nerve Regeneration, Tissue Engineering: Part A, 25(11-12):887-900 (2019).
Rajan, et al., Conditioned medium from human gingival mesenchymal stem cells protects motor-neuron-like NSC-34 cells against scratch-injury-induced cell death, International Journal of Immunopathology and Pharmacology, 30(4):383-394 (Oct. 2017).

\* cited by examiner

| | |
|---|---|
| Gum | CD90 = 30,2%<br>CD105 = 1,5%<br>CD73 = 24,2%<br>CD63 = 6,9%<br>CD146 = 20,7%<br>KRT5 = 4,90% |
| Passage 0 | CD90 = 96,1%<br>CD105 = 98,5%<br>CD73 = 99,9<br>CD63 = 80,4%<br>CD146 = 30,4%<br>KRT5 ≤1% |
| Passage 1 | CD90 = 99,6%<br>CD105 = 99,3%<br>CD73 = 100,0<br>CD63 = 98,7%<br>CD146 = 15,3%<br>KRT5 ≤1% |
| Passage 2 | CD90 = 99,5%<br>CD105 = 99,4%<br>CD73 = 99,9<br>CD63 = 98,3%<br>CD146 = 20,9% |
| Passage 3 | CD90 = 99,1%<br>CD105 = 99,7%<br>CD73 = 100<br>CD63 = 95,6%<br>CD146 = 13,4% |
| Passage 4 | CD90 = 99,7%<br>CD105 = 99,8%<br>CD73 = 100<br>CD63 = 98,2%<br>CD146 = 13,3% |
| Passage 5 | CD90 = 99,2%<br>CD105 = 98,9%<br>CD73 = 99,8<br>CD63 = 91,0%<br>CD146 = 6,2%<br>KRT5 ≤1% |

FIG. 3

| Source | Culture Medium | CD90 | CD105 | CD73 | CD63 | CD146 | Proliferation Index |
|---|---|---|---|---|---|---|---|
| GF - H004 | DMEM (Glu) + Lysat 3% + Heparine + MEM NEAA | 96,60 | 96,50 | 96,50 | 80,00 | 2,70 | 5,4 |
| GF - H004 | DMEM (Glu) + Lysat 3% + Heparine | 96,10 | 96,00 | 96,10 | 82,80 | 3,40 | 9,1 |
| GF - H004 | SCARCELL Medium | 99,30 | 98,20 | 99,30 | 96,30 | 3,00 | 17,5 |
| GF - H004 | DMEM (Glu) + Lysat 3% + Heparine + MEM NEAA | 96,10 | 94,70 | 96,00 | 65,80 | 3,30 | 5,3 |
| GF - H004 | DMEM (Glu) + Lysat 3% + Heparine | 95,00 | 93,10 | 95,00 | 71,60 | 4,80 | 5,1 |
| GF - H007 | SCARCELL Medium | 97,5 | 96,4 | 97,6 | 93,5 | 0,2 | 15,7 |
| GF - H007 | SCARCELL Medium | 99,40 | 99,10 | 99,40 | 97,90 | <1 | 21,7 |

FIG. 4

| 14/11/2022 SCARCELL01 - P4 (2T175) |||
|---|---|---|
| Phenotype | | Number |
| CD90 | 99,9% | 45,12.10$^6$ |
| CD105 | 96,7% | |
| CD73 | 99,8% | Viable |
| CD63 | 96,5% | 98,7% |
| CD146 | 27,9% | |

Without Non Essential Amino Acid | With Non Essential Amino Acid

| SCARCELL01 - P5 W/O AA |||
|---|---|---|
| Phenotype | | Number |
| CD90 | 100% | 4.10$^6$ |
| CD105 | 98,2% | |
| CD73 | 100% | Viable |
| CD63 | 96,5% | 94,8% |
| CD146 | 74,4% | |

| SCARCELL01 - P5 WITH AA |||
|---|---|---|
| Phenotype | | Number |
| CD90 | 100% | 11,5.10$^6$ |
| CD105 | 99,4% | |
| CD73 | 100% | Viable |
| CD63 | 95,8% | 96,3% |
| CD146 | 52,7% | |

| SCARCELL01 - P6 WITH AA |||
|---|---|---|
| Phenotype | | Number |
| CD90 | 99,9% | 5.10$^6$ |
| CD105 | 97,7% | |
| CD73 | 100% | Viable |
| CD63 | 96,2% | 98,6% |
| CD146 | 47,4% | |

| SCARCELL01 - P6 W/O AA |||
|---|---|---|
| Phenotype | | Number |
| CD90 | 100% | 9,4.10$^6$ |
| CD105 | 96,7% | |
| CD73 | 99,9% | Viable |
| CD63 | 97,2% | 97,6% |
| CD146 | 14,2% | |

| SCARCELL01 - P7 W/O AA |||
|---|---|---|
| Phenotype | | Number |
| CD90 | 99,9% | 4,7.10$^6$ |
| CD105 | 97,7% | |
| CD73 | 100% | Viable |
| CD63 | 88,4% | 99,0% |
| CD146 | 25,8% | |

| SCARCELL01 - P7 WITH AA |||
|---|---|---|
| Phenotype | | Number |
| CD90 | 99,9% | 13,4.10$^6$ |
| CD105 | 97,4% | |
| CD73 | 99,9% | Viable |
| CD63 | 96,7% | 96,7% |
| CD146 | 18,3% | |

| Subject reference | Lesion grade | Deformation after injection | Ultrasound evolution at 3 months | Ultrasound evolution at +6 months |
|---|---|---|---|---|
| EC1_1 | 2 | D1 | B | Recurrence (7 months) |
| EC1_2 | 3 | D1 | A | Donated horse |
| EC1_3 | 3 | D0 | B | A - recurrence after |
| EC1_4 | 3 | D0 | A | A - recurrence at 10 months |
| EC1_5 | 2 | D2 | A | A |
| EC1_6 | 3 | D1 | C | A |
| EC1_7 | - | - | B | A⁻ |
| EC1_8 | 3 | D1 | A | A |
| EC1_9 | 3 | D2 | B | |
| EC1_10 | 3 | D3 | A | A - recurrence at 9 months |

| Lesion grade | |
|---|---|
| 0 | normal echogenicity |
| 1 | discrete hypo-echogenicity |
| 2 | mixed 50/50, hypoechoic and isoechoic |
| 3 | predominantly hypoechoic |
| Ultrasound grade evolution | |
| A | complete disappearance of the hypoechoic zone |
| B | heterogeneous appearance and persistence of some hypoechoic foci |
| C | persistence of a hypoechoic lesion with more than 50% filling |
| D | persistence of a hypoechoic lesion with less then 50% filling |
| E | no ultrasound evolution |
| Deformation After Injection | |
| D0 | absent |
| D1 | discrete |
| D2 | moderate |
| D3 | marked |

MAMMALIAN CELL POPULATION AND MEDICAMENTS FOR CELL THERAPIES IN EQUINES AND IMPROVED CELL CULTIVATION METHODS

CROSS-REFERENCE TO RELATED APPLICATIONS

This application claims priority to U.S. Provisional Patent Application Ser. No. 63/290,489, filed Mar. 15, 2023 and EP patent application Ser. No. 23/305,350.3, filed Mar. 15, 2023, the entire contents of each of which are incorporated herein by reference.

FIELD OF THE INVENTION

The present invention relates generally to compositions of matter and medicaments derived from gingival fibroblasts to use in cell therapies and improved methods for cultivating such compositions to create specialized phenotype populations that advantageously vary from naturally occurring tissue. In particular, the inventive methods are designed to enhance cell proliferation to facilitate generation of the inventive cell compositions in sufficient quantities to realize commercial scale production. Also included are methods of using the novel composition to treat a variety of mammalian afflictions, including those affecting epi- and endo-thelial surfaces (e.g., skin-aging, pressure ulcers, alopecia, immune and vascular diseases) and of osteopathic origin (e.g., osteoarthritis, cartilage defects, etc.).

BACKGROUND

For at least the last two decades, uses of gingival fibroblasts have been investigated for a wide range of cell therapy treatments due to the multipotent nature of gingival fibroblasts and the ability of such cells to differentiate into a broad spectrum of cells than other types of mesenchymal stem cells. In addition, while the latter are harvested from bone marrow, which poses some risks to the donor, gingival fibroblasts are readily harvested from gum tissue, e.g., during wisdom tooth extraction and other dental procedures.

Use of gingival fibroblast (GF) derived compositions, both cultured GF cells and GF conditioned media, have been described for treatment of a number of mammalian ailments, as set forth in the following U.S. patents and publications: U.S. Pat. No. 8,609,085 (atherosclerosis); U.S. Pat. No. 8,303,948 (skin wounds); U.S. Patent Application Publication No. 2011/0097421 (skin aging); U.S. Pat. No. 10,624,838 (alopecia); U.S. Pat. No. 11,229,670 (allergic reactions, atopic dermatitis and asthma); U.S. Patent Application Publication No. 2018/0028571 (cancer); U.S. Patent Application Publication No. 2016/0256496 (human orthopedic pathologies, including osteoarthritis and cartilage defects); U.S. Patent Application Publication No. 2020/0268805 (equine musculoskeletal diseases, including tendinitis, arthropathy and arthrosis) and International Publication No. WO2023/007244A1 (pressure ulcers). All of following patents and applications are licensed or assigned to the assignee of the present application, the entireties of which are incorporated herein by reference.

Methods of cultivating gingival fibroblasts are described in a number of previously known articles, including for example, Hou et al., "Autologous Transplantation of Gingival Fibroblast-Like Cells and a Hydroxylapatite Complex Graft in the Treatment of Periodontal Osseous Defects: Cell Cultivation and Long-Term Report of Cases," Cell Transplantation, 12:787-797 (2003); Ferré et al., "Formation of Cartilage and Synovial Tissue by Human Gingival Stem Cells," Stem Cells & Dev., 23(23):2895-2907 (2014); Linard et al., "Therapeutic Potential of Gingival Fibroblasts for Cutaneous Radiation Syndrome: Comparison to Bone Marrow-Mesenchymal Stem Cell Grafts," Stem Cells & Dev., 24(10): 1182-1193 (2015) and Ahangar et al., "Human gingival fibroblast secretome accelerates wound healing through anti-inflammatory and pro-angiogenic mechanisms," npj Regenerative Medicine 5(24)1-10 (2020). All of the foregoing articles describe previously known methods of cultivating cells, including use of at least a culture medium, e.g., Eagle's minimally essential medium (EMEM) or Dulbecco's Modified Eagle's Medium (DMEM), an antibiotic (e.g., penicillin, streptomycin or gentamicin), and a mammalian blood derived serum, such as 10% Fetal Bovine Serum (FBS).

In general, previously known methods of cultivating gingival fibroblasts involved explanting gum tissue, followed either by mincing or enzymatic digestion. Cells then are incubated in a medium as described above in a humidified incubator with 5% carbon dioxide atmosphere for a period of about two to three weeks until confluence is attained, and then trypsinized to create single cell suspensions. In some cultivation methods, the culture medium may be refreshed every 72 hours and after the initial cultivation period, gingival fibroblast colonies may again be trypsinized to create single cell suspensions that are seeded in fresh culture for additional two week periods, often referred to as "passages." After a final passage and trypsinization step, the cultivated cells may be washed and collected for use in a desired application.

A number of drawbacks exist for previously known cultivation methods and the resulting cell compositions. One such drawback is the time required to cultivate a small number of gingival fibroblasts to create cell colonies in large enough scale to support a commercial application. In particular, it would be desirable to provide cell compositions, and methods for cultivating such compositions, that enhance proliferation during the cultivation stage. In this manner, cell populations sufficient for commercialized methods of treating the disease states described in the above-incorporated patents may be realized, thereby assisting in transitioning the use of gingival fibroblasts from an investigational laboratory technology to commercial scale practical treatment applications.

Another drawback of previously known compositions and methods has been the inability to tailor the protein expression characteristics of cell phenotypes in the cultivated cell populations. For example, it is known that natural gingival fibroblasts when cultured in vitro will contain large populations of cells that express CD146, also referred to as melanoma cell adhesion molecule, which is associated with melanoma cell tumorigenicity. It therefore would be desirable for many of the treatments described in the above-incorporated patents and applications to restrict phenotypes that express CD146. Similarly, it would be desirable to cultivate the gingival fibroblast cells to enhance the expression of certain phenotypes, such as CD90, also known as THY1, and TIMP1, the latter of which inhibits the production of matrix metalloproteinases and reduce inflammatory reactions.

In view of the foregoing, it would be desirable to provide compositions and medicaments derived from gingival fibroblasts that include cell populations cultivated to have specific protein expression phenotypes, in which the phenotypes preferentially are selected to express proteins favoring angiogenesis and anti-inflammatory effects, while reducing cell populations that promote tumorigenicity and/or formation of metalloproteinases that inhibit tissue regeneration.

It further would be desirable to provide compositions, medicaments and methods for cultivating such compositions in sufficient quantities to facilitate methods of use of the compositions in treating a variety of mammalian diseases, including, but not limited to, atherosclerosis, skin wounds, skin aging, alopecia, allergic reactions, atopic dermatitis, asthma, pressure ulcers, cancer, orthopedic pathologies, including osteoarthritis and cartilage defects, tendinitis, arthropathy and arthrosis.

SUMMARY OF THE INVENTION

The present invention is directed to compositions, medicaments and methods of producing compositions of gingival fibroblasts having phenotypes cultivated to express preferred proteins. In particular, the cell populations of the gingival fibroblasts of present invention differ from gingival fibroblasts occurring in native gum tissue in that the cell phenotypes preferentially are selected to express proteins favoring angiogenesis and anti-inflammatory effects, while reducing cell populations that promote tumorigenicity and/ or formation of metalloproteinases that inhibit tissue regeneration. In one embodiment, the composition differs from the cell population of natural gingival fibroblasts by having a cell population, or conditioned media, in which at least about 90% of the cells have a phenotype of expression of THY1, CD99 or CD63, and about 20% or less of the cells have a phenotype of expression of CD146.

In accordance with a further aspect of the invention, methods are provided for cultivating a composition having the above-specified phenotype characteristics that enhance cell proliferation to make practical generation of commercial scale quantities of the composition. In particular, the methods of the present invention advantageously not only enable preferential selection of cell phenotypes, but permit cultivation at substantially increased rates of cell proliferation. In one preferred embodiment, the cell cultivation process includes multiple passages of the cells in 20% FBS with non-essential amino acids and frequent culture media changes, resulting in more than doubling the cell proliferation compared to prior art cultivation methods.

Further in accordance with the invention, methods of using the inventive compositions and medicaments are provided for treating an array of mammalian maladies, including atherosclerosis, skin wounds, skin aging, alopecia, allergic reactions, atopic dermatitis, asthma, cancer, human orthopedic pathologies, including osteoarthritis and cartilage defects, tendinitis, arthropathy and arthrosis and pressure ulcers. The cultured gingival fibroblasts and conditioned media of the present invention also may be useful in regenerating resected or injured nerves, e.g., spinal cord injuries. Based on preliminary animal data, it has been observed that response to the foregoing treatments may be dose dependent, such that to obtain a clinical significant and durable treatment response, the treatment should deliver a cell population of between 5 and 40 million cells to a treatment site, and more preferably, about 20 million cells.

The compositions of the present invention may comprise an cultured mammalian cell population as defined above in a liquid cell culture medium, or a medicament derived from the cultured mammalian cell population as defined above, or a pharmaceutical or cosmetic composition comprising the cultured mammalian cell population as defined above, including at least one pharmaceutically or cosmetically acceptable carrier or excipient.

Other features of the inventive system and methods will be apparent with reference to the following description and figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a table showing evolution of the gingival fibroblast phenotypes in the cultured cell population during five cultivation passages in accordance with the principles of the present invention.

FIG. 4 is a table showing representative the protein expression characteristics and proliferation indices for various conventional culture media compared to that of the present invention.

FIG. 7 is a chart showing the effect on cell population phenotypes arising from cultivating gingival fibroblasts with and without non-essential amino acids during additional cultivation passages.

FIG. 11 is a table showing summary results for data obtained in for a first equine group at ninety days after injections of a composition according to the present invention to treat fetlock arthropathy.

DETAILED DESCRIPTION OF THE INVENTION

The present invention is directed to compositions of matter, including cell populations and medicaments, derived from gingival fibroblasts having phenotypes that occur in proportions not found in natural gum tissue. The present invention further provides methods of generating such compositions, and methods of using such compositions and conditioned media in a wide range of mammalian cell therapies, including humans, canines and equines.

Compositions and Medicaments of the Invention

Compositions in accordance with the principles of the invention preferentially includes cell populations that express angiogenic and anti-inflammatory proteins, and have few cells of phenotypes that express proteins associated with tumorigenicity or encourage formation of metalloproteases. The cell populations are cultivated from gingival fibroblasts, as described below, to have phenotype proportions different that those occurring in natural gum tissue. The inventive cell populations may be packaged directly for use as medicaments, or used to create conditioned media for use as medicaments.

In preferred embodiments, the composition includes about 10% or less of the cells of the cultured mammalian cell population the express at least one mRNA selected from the group consisting of CD146, also known as a melanoma cell adhesion molecule (MCAM), VCAM1, CD19, ITGAM, CD3D, CD4, FZD9, NGFR, NANOG, POU5F1, SOX2, KLF4, MYC, TNF, IL1A, IL1B, IL17A, IL23A, OSM, IFI27, IFI44L, RSAD2, IFIT1, IFNA1 and IFNG mRNAs.

Preferably, at least about 50% of the cells of the cultured mammalian cell population express at least one mRNA selected from the group consisting of TIMP1, CD9, CD81, THY, ITGB1, FST, and COL1A2 mRNAs, more preferably at least about 90% of the cells of the cultured mammalian cell population express CD63 mRNA and the TIMP1 mRNA. TIMP1 stands for TIMP metallopeptidase inhibitor 1.

Figure 1:
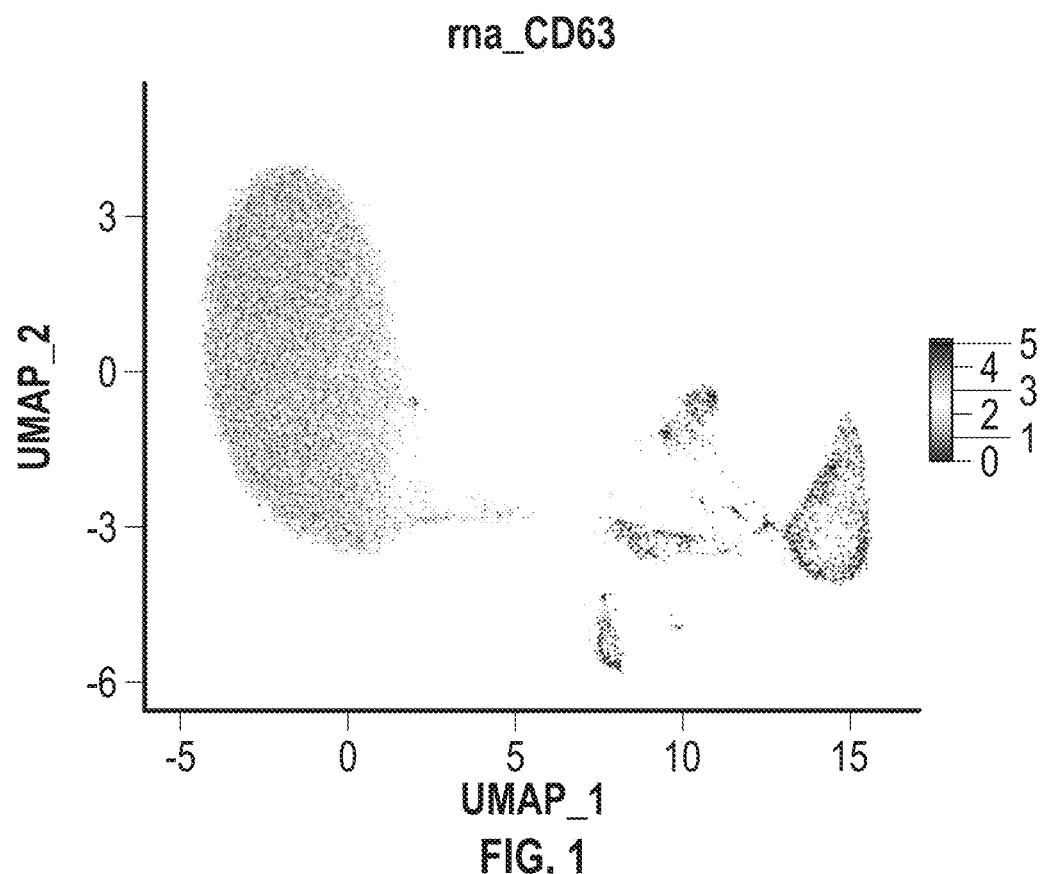
FIG. 1 is a uniform manifold approximation and projection plot comparing the protein expression characteristic of cultured gingival fibroblasts in accordance with the methods of the present invention to protein expression of natural gum tissue for the CD63 antibody.
Figure 2:
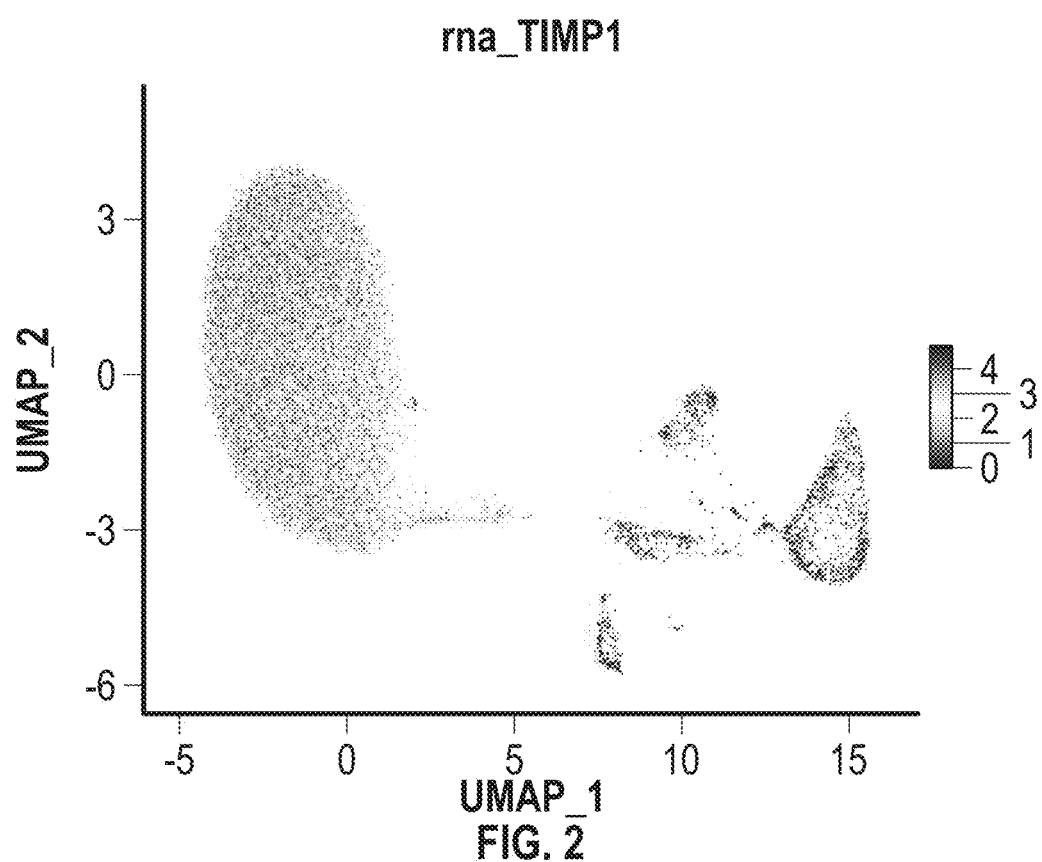
FIG. 2 is a uniform manifold approximation and projection plot comparing the protein expression characteristic of cultured gingival fibroblasts in accordance with the methods of the present invention to protein expression of natural gum tissue for the TIMP1 antibody.

Referring to FIGS. 1 and 2, exemplary plots show the protein expression characteristics (as measured by mRNA transcripts) for the cultured gingival fibroblasts according to the invention for CD63 and TIMP1, denoted by the elliptical cluster on the left hand side of the plot, compared to the scattered clusters for these proteins generated by natural gum tissue. As described below, the inventive methods of cultivating the gingival fibroblasts over several cultivation passages preferentially enhances desired phenotypes while limiting the growth of less desirable phenotypes.

FIG. 3 is a chart showing evolution of specific cell protein expression phenotypes cultivated from human gingival fibroblasts during multiple passages to generate a cell population according to the present invention. In particular, the phenotype proportions for naturally occurring gum tissue include populations wherein only 30.2% of cells express desirable CD90 proteins and 6.9% express desirable CD63, while 20.7% express the less desirable CD146 protein, a melanoma cell adhesion molecule. However, as indicated in subsequent cultivation passages 0 to 5, the proportion of desired phenotypes preferentially is increased, while proliferation of undesired phenotypes is restricted. For example, by completion of passage 2, the proportion of cells the express CD90, CD105, CD73 and CD63 proteins all exceed 95%, while the proportion of cells that express CD146 is a 13.4%. However, during the next two passages, the proportion of cells expressing CD146 is reduced by more than half, to 6.2%, without significantly reducing the proportion of cells that express CD90, CD105, CD73 and CD63 proteins.

Preferably, essentially all the cells of the cultured mammalian cell population have an undifferentiated phenotype, more preferably a fibroblast-like phenotype. The cultured mammalian cell population preferably originates from a mucosa, more preferably from the oral mucosa, in particular from the mucosa of the cheek, of the tongue, of the palate, of the labial mucosa, of the sublingual mucosa, or of the gingiva. The procedure for taking a sample or a biopsy from a mucosa is well known to the person skilled in the art. Generally, the cells of the biopsy are separated by enzymatic digestion before being expanded.

Suitable cultured mammalian cell populations may derive from any mammal, such as a domestic animal, e.g. selected from the group consisting of an equine, in particular a horse, of a camelid, in particular a camel, a dromedary or a llama, of a bovine, of a caprine, of a canine, in particular a dog, of a feline, in particular a cat, and of a Mustelidae. It is preferred for compositions intended for use in humans that the cultured mammalian cell population be obtained from a human cell population. The cell population according the invention may be autologous or heterologous. As one of skill in the art will understand, the individual from whom the cells are taken and the individual to whom the cells are administered are preferably of the same species, however they can be of different species.

The cell population can present in various forms, such as a suspension in a liquid, e.g. a physiological solution, PBS or a cell culture medium, a culture on a solid culture medium, or a pellet, in particular a centrifugation pellet.

As used herein, a composition or medicament according to the invention comprises the cell population according to the invention in a prophylactically or therapeutically effective amount. Preferably, the composition according to the invention comprises from 5 million to 40 million cells according to the invention, more preferably from 10 million to 30 million cells according to the invention, even more preferably from 15 to 25 million cells according to the invention, and most preferably about 20 million cells according to the invention. The quantification of the cells according to the invention may be performed by any method for counting mammalian cells known to one of skill in the art, for example, a cell counter machine.

The composition or medicament may be in any form suitable for its intended application. In a preferred embodiment of the invention, the composition may be an injectable form, e.g., suitable for delivery via injection with a syringe. In an alternative embodiment, the composition may be in a form suitable for topical administration. In that case, the composition preferably may be in the form of a lotion, cream, ointment, gel, spray, wipe, dressing, pad or patch.

As used herein, a "conditioned media" product is derived from the inventive mammalian cell population may be any product obtained from the cell population in itself or that contains secretions from the cell population. Preferably, the conditioned media product derived from the cultured mammalian cell population is a cell extract. The extract may be obtained by any cell fragmentation method known in the art, including from the group consisting of a membrane extract, a cytoplasmic extract or a nuclear extract.

Conditioned media according to the invention further may include a liquid cell-culture medium that has been contacted by cells of the inventive cell population, in particular, for a time sufficient for the cells to have secreted in the medium. Thus, the conditioned medium according to the invention contains secretions of cells of the cultured mammalian cell population according to the invention. Preferably, the cells are put in contact with the culture medium for at least 2, 4, 6, 8, 10, 12, 24, 36 or 48 hours, and generally less than 56 or 72 hours.

Conditioned media according to the invention may be subjected to treatment steps such as centrifugation, filtration, or concentration. In particular, the conditioned medium according to the invention may be a concentrated conditioned medium, more particularly a conditioned medium concentrated 2, 5, 10, 25 or 50 times with respect to the unconcentrated conditioned medium from which it derives.

Described herein are cells, cell populations, phenotypes, and the like which express or do not express an indicated protein or mRNA. In accordance with the present disclosure, an indicated cell is deemed to not express the indicated protein or mRNA when a standard laboratory assay (e.g., single nuclei RNA-sequencing method (snRNAseq), such as that substantially described by Grindberg et al., *Proc. Natl Acad. Sci. USA* 110:19802-19807 (2013), Fluorescence Activated Cell Sorting (FACS), etc.) fails to detect appreciable levels of the protein or mRNA. Conversely, a cell is deemed to express the indicated protein or mRNA when the method does detect an appreciable level of the protein or mRNA.

As will be appreciated by one of skill in the art, protein expression can be measured in accordance with the instant disclosure by measurement of a corresponding mRNA transcript.

Cultivation of the Preferred Cell Populations

In accordance with one aspect of the invention, gingival fibroblasts are cultivated through five to seven passages after extraction from natural gum tissue to preferentially adjust the phenotypes in the composition, thereby increasing desirable protein expression characteristics while suppressing undesirable protein expression characteristics.

In one embodiment, heterologous mammalian gum tissue is harvested from the oral cavity of a suitable mammal of the species in which the cultured cells composition, or conditioned media, eventually will be used. The harvested tissue is cut by scalpel into small fragments, and the fragments are enzymatically digested. The dissociated cells are washed in a phosphate buffered saline (PBS) and a cell suspension created by placing the washed cells in a mixture of culture medium and 20% FBS. By way of example, suitable culture medium according to the invention includes Eagle's Minimum Essential Medium (MEM or EMEM), Eagle's Minimum Essential Medium Alpha Modification (Alpha MEM) and Basal Medium Eagle (BME).

Next, a zero cultivation passage at a cell seeding density of 10,000 cells per $cm^2$ is conducted, in which the cells are cultivated in a culture flask with a culture medium, 20% FBS, an antibiotic, Basic Fibroblast Growth Factor (bFGF). Basic Fibroblast Growth Factor (bFGF) refers to human bFGF, and more preferably to recombinant human bFGF produced in *Escherichia coli* having the sequence identified in SEQ No. 1, a listing of which is set forth in U.S. Pat. No. 7,951,593, which is incorporated herein by reference. The medium is removed, the cells are washed with PBS, on days 3 and 10. On day 21, the medium is removed, the cells again are washed with PBS, and trypsinized to remove them from the flask. By completion of the zero passage, after 21 days, the gingival fibroblast population generally will have expanded to 6 fold.

In a first passage, the cells in a mixture of culture medium, 20% FBS and bFGF and cultivated in culture flasks at 37 C with an atmosphere of 95% oxygen and 5% carbon dioxide at 95% humidity at a cell seeding density of 4,500 cells per $cm^2$. On day 3, the cells are washed with PBS, a fresh mixture of culture medium, 20% FBS and bFGF is provided, and the cells cultivated for another 3 days, after which the cells are again trypsinized. During the first passage of 6 days, a cell population generally will have expanded about 15 fold, e.g., in an exemplary embodiment, from about 10 million cells to about 143 million cells. After a further wash with PBS, the cells are placed in a storage medium consisting of about in a solution of human serum albumin 4% w/v (USP/Ph.Eur) and 10% DMSO (USP/Ph.Eur), and may be stored in quantities of 10 million cells per storage tube.

In a second passage, the cells from a single storage tube are dispersed in a mixture of culture medium, 20% FBS and bFGF at a cell seeding density of 4,500 cells per $cm^2$, which is renewed after 4 days. On day 7, the culture medium mixture is removed. At the completion of passage 2, the cells generally again will have expanded about 15 fold.

In a third passage, cells are seeded at density 4,500 cells per $cm^2$ in, for example, a multi-plate bioreactor or other similar device for large scale expansion, with a mixture of culture medium, 20% FBS and bFGF. The culture medium mixture is replaced with a fresh mixture after 3 days, and cultured for another 3 days. After 6 days, the cells are trypsinized, rinsed in PBS and placed in storage tubes with a storage medium consisting of about in a solution of human serum albumin 4% w/v (USP/Ph.Eur) and 10% DMSO (USP/Ph.Eur). At the completion of passage 3, the cells generally will have expanded to about 15. Preferably, the cells may be distributed for storage in tubes holding about 10 million cells each.

In a fourth passage, the cells from a single storage tube are dispersed in a mixture of culture medium, 20% FBS and bFGF at a cell seeding density of 4,500 cells per $cm^2$, which is renewed after 4 days, washed with PBS and placed in a bioreactor for a fifth passage of another 6 days, following the protocol of the second passage. At the completion of the fourth passage, the cells generally will have expanded about 15 fold and are trypsinized, washed with PBS, prepared for further cultivation in a fifth passage.

In the fifth passage, cells are seeded at density 4,500 cells per $cm^2$ in bioreactors, or other large scale expansion device, with a mixture of culture medium, 20% FBS and bFGF, which is replaced with a fresh mixture of culture medium after 3 days. On day 3, the culture medium mixture is removed is replaced with a fresh culture medium mixture that omits fetal bovine serum and adds Interleukin 1 Beta (IL-1ß). One day later, the culture medium mixture is removed and the cells generally will have expanded about 15 fold and trypsinized, rinsed with PBS, and stored in storage tubes holding 10 million cells each with a storage medium as described above.

Preferably, as described above, the cell population of the invention is cultivated during the fifth passage in the presence of an inflammatory cytokine, such as IL-1β, prior to being used in a therapeutic or cosmetic application according to the invention. The concentration of the inflammatory cytokine, in particular IL-1β, in the culture medium can be from 0.1 ng/ml to 10 ng/ml, more preferably from 0.5 ng/ml to 2 ng/ml. The inflammatory cytokine, in particular IL-1β, can be retrieved from the cell culture, e.g. by washing the cells, before use in a therapeutic or cosmetic application according to the invention.

The cell culture of the invention can be concentrated e.g. by filtration or by centrifugation. In particular, the cell culture can be concentrated 2, 5, 10, 25 or 50 times with respect to the unconcentrated cell culture from which it derives.

Cultivation of a composition according to the present invention by the process described above results in an exemplary cell population having the protein expression characteristics described in FIG. 3. While not intending to be limiting, key differences in the process of cultivating gingival fibroblasts in accordance with the present invention, as compared to the cultivation methods described in the previously known methods include employing 20% FBS and basic fibroblast growth factor during the cell cultivation, and replacing the culture medium mixture about every at predetermined times during multiple six to seven day passages. In addition, the methods further include employing IL-1ß and/or non-essential amino acids during the final passages to adjust the protein expression characteristics of the target cell population, as demonstrated in FIGS. 1-3.

Referring now to FIG. 4, another key aspect of the invention is the ability of the process described above to enhance cell proliferation during the cultivating process. This index, also referred to as an expansion index, indicates how many fold the cells have expanded during a specified passage. It has been observed that, relative to methods of cell cultivation described in the above literature, the methods of the present invention achieve a significantly greater proliferation. This, in turn, permits the composition of the present invention to be generated in quantities, within a specified period, sufficient to support commercial application. Specifically, FIG. 4 reports results achieved after five cultivation passages using conventional culture medium that include 10% FBS, and Scarcell medium. An exemplary formulation of the latter, as described above, is DMEM, 20% FBS, and bFGF. While not intending to be limiting as to the method of action, it is hypothesized that the use of a higher concentration of fetal bovine serum, and frequently replacing it, maintains the stability of the cell culture.

For conventional media, consisting of various combinations of DMEM, Lysat 3%, Heparine, and 10% FBS, with and without Non-essential Amino Acids, FIG. 4 shows that the proliferation index varied from about 5-fold to 9-fold. By comparison the results achieved with the Scarcell medium was 17 fold for one source of gingival fibroblasts and up to 22 with another. In addition, the method according to the present invention, as described above, enhances the yield of cells that desirably express the CD63 protein between about 20 to 50%. These results demonstrate a two-to-three times greater ability to expand gingival fibroblasts during cultivation, thus offering a path towards greater supply of the inventive composition during a specified period, and potentially reduced costs for such production.

Figure 5:
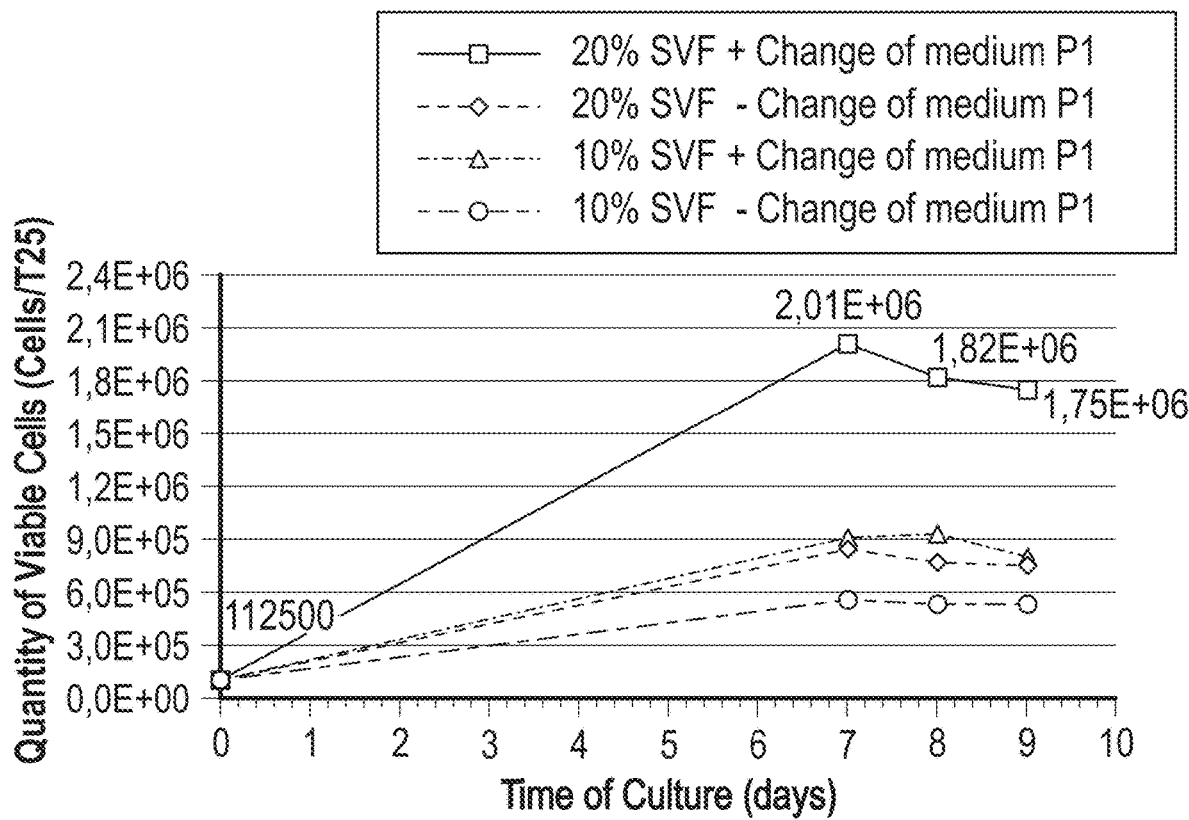
FIG. 5 is a chart showing the effect of using different concentrations of FBS during cell culture, and changing the culture medium during a first passage of the cell cultivation.
Figure 6:
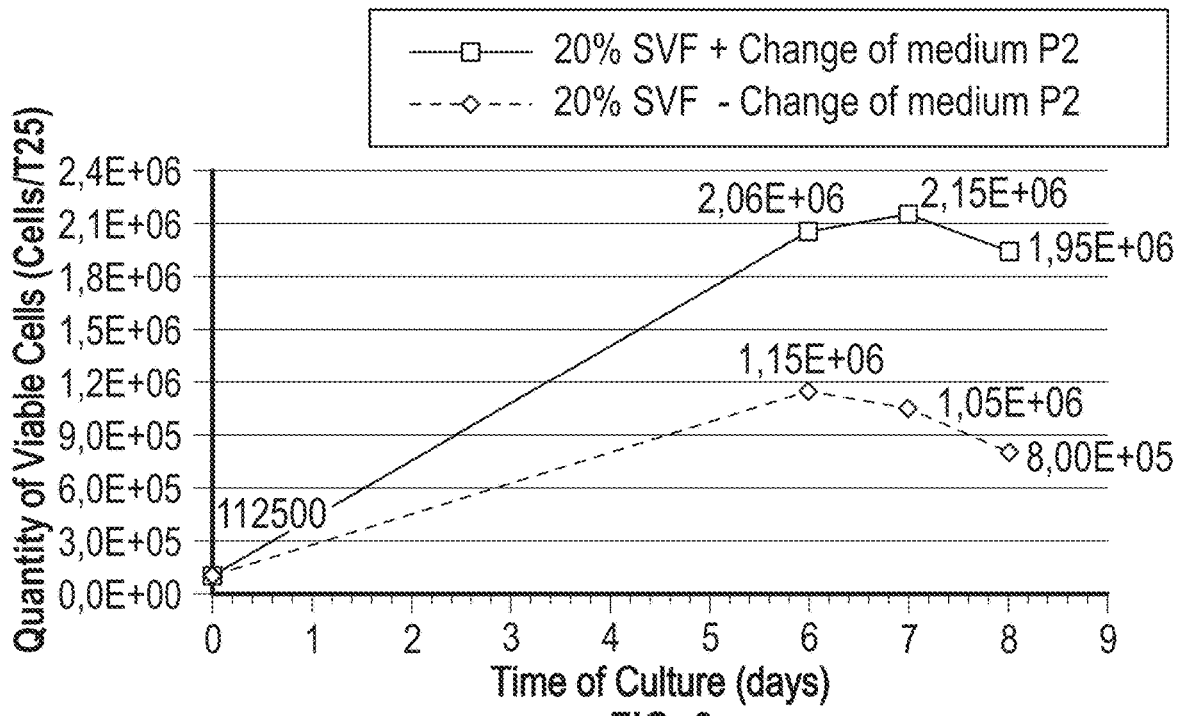
FIG. 6 is a chart showing the effect of changing the culture medium during a second passage of the cell cultivation.

Referring now to FIGS. 5 and 6, graphs depicting gains in gingival fibroblast populations as a function of time and culture medium are described. In particular, the lines denoted by open squares (□) and triangles (▲) in FIG. 5 show the evolution of the cell quantities cultivated during a first passage in a medium having 10% FBS. The line denoted by the triangles (▲) correspond to cultivations in which the culture medium was replaced after the first 4 days, while the line denoted by open squares (□) corresponds to no replacement of the culture medium. In FIG. 5, lines denoted by diamonds (♦) and closed squares (■) show the evolution of the cell quantities cultivated during a first passage in a medium having 20% FBS, where the medium was replaced after the first four days, closed squares (■), or was not replaced, diamonds (♦). All four lines in FIG. 5 show that the viable cell quantities stagnate or decline after 7 days of cultivation, with the 10% FBS medium (with medium replacement) providing about the same cell count as achieved using 20% FBS, without replacement. Unexpectedly, however, using 20% FBS while also replacing the medium after the first 4 days results more than doubles the number of viable cells after 7 days of cultivation.

FIG. 6 provides results similar to that shown in FIG. 5, but for a second cultivation passage conducted in culture medium with 20% FBS. Specifically, in FIG. 6, the line denoted by diamonds (♦) correspond to a medium having 20% FBS, wherein the medium was not changed after 4 days, and the line denoted by closed squares (■) show the evolution of the cell quantities cultivated in a medium having 20% FBS, where the medium was replaced after the first four days. As shown in FIG. 6, the number of viable cells where the medium is not replaced begins to decline after six days, and begins to level off after 7 days where the medium is replaced. Notably, and unexpectedly, changing the medium after the first 4 days during the second cultivation passage about doubles the yield of viable cells during the second passage.

Turning now to FIG. 7, an alternate implementation of the process according to the present invention is described, in which one or more additional cultivation passages are completed to reduce the cell population that expresses the undesirable protein, CD146. In this method, cells completing the fourth passage, as described above, are cultivated for a fifth, sixth and optional seventh passage, substantially as described above, except with the addition of Non-Essential Amino Acids added to the culture medium. As shown in FIG. 7, the percentage of cells that express the CD146 protein increase from 27.9% at the conclusion of the fourth passage, increases to 52.7% in the fifth passage, then 14.2% in a sixth passage when cultivated with NEAA. By comparison, omitting NEAA from the culture medium during the fifth passage increases the percentage of cells expressing CD146 to 74.4%, which is reduced only to 25.8% after two additional passages. Accordingly, the methods of the present invention preferably include adding NEAA in the culture medium during later passages of the cell cultivation process, specifically to adjust the proportions of the cell population to alter protein expression characteristics.

Therapeutic Uses of the Inventive Compositions

Cell cultures and conditioned media prepared in accordance with the principles of the present invention may advantageously be used for treating a wide variety of mammalian diseases, as described in the above-incorporated commonly assigned or licensed patents and publications. For example, cultured cell suspensions or conditioned media products derived therefrom may be used for treating atherosclerosis, skin wounds, skin aging, alopecia, allergic reactions, atopic dermatitis, asthma, cancer, human orthopedic pathologies, including osteoarthritis and cartilage defects, tendinitis, arthropathy and arthrosis and pressure ulcers. Compositions and conditioned media of the present invention also may be used to regenerate nerve tissues, e.g., to treat spinal cord injuries. Administration of the cultured mammalian cell population as defined above or the conditioned medial product derived from the cultured mammalian cell population as defined above, or pharmaceutical composition derived therefrom, may proceed by any method known in the art, including administered subcutaneously, intravenously, intramuscularly, intra-dermally or topically, near or on the skin area to be treated.

For example, skin-related disorders may be treated by topical application of the composition or conditioned media, while vascular diseases may be treated by intravascular injection or delivery of stents or other devices having reservoirs from which the composition may be delivered. Still other applications, such osteopathic treatments, may involve direct injection into the joint or vicinity of the tendon.

Surgical wounds are wounds voluntarily made during a surgical procedure. Such surgical wounds notably encompass wounds occurring in the course of plastic and reconstructive surgery or scar revision wounds (e.g. hypertrophic scars). The plastic and reconstructive surgery procedures can be of any type, e.g. breast surgery, abdominal surgery, nose surgery, car surgery, or removal of skin defects. As intended herein, skin defects relate to an abnormal skin formation found in genetically predisposed individuals, or to the consequences of an abnormal skin development during embryogenesis, and notably comprise giant naevi, cheiloschisis, and keloids.

As intended herein "treating a skin wound" relates to the promotion, the acceleration, or the improvement of healing at the wounded site, i.e. the formation of a functional skin at the wounded site. As intended herein a "functional skin" relates to skin having in particular recovered its mechanical properties and its barrier function, with respect to non-wounded skin areas. An inflammatory skin lesion generally is due to an inflammatory skin disease, in particular to a chronic inflammatory skin disease, and may include the group consisting of dermatitis, inflammatory skin rash, ichthyosis and psoriasis. Chronic inflammatory disease also includes rheumatoid arthritis, lupus erythematosus and multiple sclerosis.

The cultured cell suspensions or conditioned media products derived therefrom also may find application in cosmetic uses. As intended herein, "cosmetically acceptable carrier or excipient" refers to any material which is suitable with a cosmetic composition. Preferably, the cosmetically acceptable carrier or excipient is suitable for a topical administration. The cosmetically acceptable carrier or excipient according to the invention include but is not limited to any of the standard cosmetic carrier or excipient known to one of ordinary skill in the art such as water, vegetal oil, mineral oil, fatty acid alcohol and natural waxes.

Example 1

Single Nuclei RNA-Sequencing of the Cell Population of the Invention

A single nuclei RNA-sequencing (snRNAseq) of the cell population of the invention, created in accordance with the described above method, was performed. The snRNAseq method was originally described in Grindberg et al., *Proc. Natl Acad. Sci. USA* 110:19802-19807 (2013) and is known to a person skilled in the art. The results of that analysis are set forth in table below.

| mRNA | Percentage of cells expressing the mRNA |
| --- | --- |
| CD99 | 55 |
| CD9 | 55 |
| CD81 | 58 |
| CD63 | 99 |
| CD47 | 19 |
| CD164 | 23 |
| CD151 | 45 |
| CD44 | 42 |
| THY1 | 70 |
| ENG | 8 |
| ITGB1 | 80 |
| ALCAM | 19 |
| FGFR1 | 14 |
| NT5E | 30 |
| MME | 21 |
| CD34 | 0 |
| PTPRC | 0 |
| MCAM | 0 |
| VCAM1 | 0 |
| CD19 | 0 |
| ITGAM | 0 |
| CD3D | 0 |
| CD4 | 0 |

-continued

| mRNA | Percentage of cells expressing the mRNA |
| --- | --- |
| FZD9 | 0 |
| NGFR | 0 |
| NANOG | 0 |
| POU5F1 | 0 |
| SOX2 | 0 |
| KLF4 | 2 |
| MYC | 4 |
| TIMP1 | 98 |
| FST | 67 |
| COL1A2 | 81 |
| FGF2 | 12 |
| TNF | 0 |
| IL1A | 0 |
| IL1B | 0 |
| IL17A | 0 |
| IL23A | 0 |
| OSM | 0 |
| IFI27 | 0 |
| IFI44L | 0 |
| RSAD2 | 0 |
| IFIT1 | 1 |
| ISG15 | 6 |
| IFNA1 | 0 |
| IFNG | 0 |

Example 2

Protein Expressed by the Cell Population of the Invention

The expression of certain proteins was determined by Fluorescence Activated Cell Sorting (FACS), as set forth in the table below.

| Protein | Percentage of cells expressing the protein |
| --- | --- |
| CD34 | <1 |
| CD45 | 6 |
| CD63 | 97 |
| CD90 | 97 |
| CD99 | 97 |

Results of Animal Studies

Initial testing of compositions produced in accordance with the methods of the present invention have been tested in canine and equine animal models, specifically including for treatment of osteoarthritis in a population of 95 dogs, and treatment of separate groups of horses afflicted with fetlock arthropathy and tendinopathy. Summaries of the results achieved during those tests is discussed with respect to FIGS. 8 to 14.

Treatment of Secondary Osteoarthritis in Dogs

Degenerative osteoarthritis is a frequent and well-known affliction in canine veterinary medicine. The disease is often triggered by damage to the subchondral soft tissue or articular cartilage, or a combination of both. This trigger leads to degradation of the articular cartilage involving bone and tissue changes. The specific origin of the lesion, e.g., inflammation of the joint or synovial lining, or a disease leading to joint degeneration, is not determinative of the outcome. Instead, synovitis generates the production of pro-inflammatory cytokines and metalloprotease, which contribute to the chronic development of the disease. In addition, synovitis causes joint pain and synovial effusions that contribute to joint instability. Prevalence in dogs varies between 2% and 20% at one year. Osteoarthritis results in significant comorbidity, associated with obesity requiring long-term treatment via administration of anti-inflammatory drugs or surgical joint replacement.

Current treatments for canine osteoarthritis have no positive impact on cartilage regeneration and primarily target symptoms, e.g., to reduce pain caused by joint inflammation. Research on alternative treatments recently has led to the development of cell-based therapies, mainly in view of the possible regenerative potential of such therapies. Current allogeneic cell therapy is limited by its half-life post-administration to subjects. The aim of the study was to evaluate the safety and efficacy of a cell therapy based on the use of allogeneic gingival fibroblast cultures in domestic dogs suffering from osteoarthritis.

A randomized study of 95 dogs was conducted using a single intra-articular injection to study the efficacy, safety and tolerability of canine gingival fibroblasts in the treatment of osteoarthritis. The injection vehicle was composed of 10% DMSO, 88% DMEM, 1% L-Glutamine, 1% non-essential amino acids for a total volume of 1 mL. Sixteen dogs received an injection of the injection vehicle (placebo) only, which contained no gingival fibroblasts, 28 dogs received an injection of 2 million cultured cells; 28 dogs received an injection of 5 million cultured cells, and 23 dogs received an injection of 10 million cultured cells. The study parameters were as follows: Inclusion criteria were moderate to severe mono- or poly-osteoarthritic dogs refractory to standard treatments; exclusion criteria included sarcoma, previous cell therapy, surgery or multiple prior injections.

The dogs were evaluated by veterinarians one month following the injections, and evaluated by the pet owners at twelve months after the injection. Lameness and pain were scored according to the following rules:

| Lameness |
| --- |
| 0 No lameness, no weight transfer at rest |
| 1 No lameness, weight transfer at rest |
| 2 Mild lameness with support at walk and trot |
| 3 Moderate lameness with support at walk, lameness without support at trot |
| 4 Severe lameness with support at walk, lameness without support at trot |
| 5 Lameness without support at walk and trot |
| Pain on palpation/patient handling |
| 0 No pain on palpation/mobilization of affected limb |
| 1 Mild pain on palpation/mobilization of affected limb (limb withdrawal) |
| 2 Moderate pain on palpation/mobilization of affected limb (head rotation) |
| 3 Severe pain on palpation/mobilization of affected limb (vocalization) |

More specifically, clinical efficacy was assessed using the Canine Brief Pain Inventory (CBPI) questionnaire as described in Brown et al., "Ability of the Canine Brief Pain Inventory to detect response to treatment in dogs with osteoarthritis," J. Am. Vet. Med. Assoc., 233(8): 1278-1283 (2008), including an assessment of the pain intensity score (CBPI questions 1-4), the pain interference score (CBPI questions 5-10), and the total CBPI score. Clinical efficacy was assessed at 1 and 12 months. Intermediate time points (three, six and nine months) were determined using the Kaplan-Meier methodology (a dog for which efficacy was observed up to six months was counted for the three and six month time points).

Figure 8:
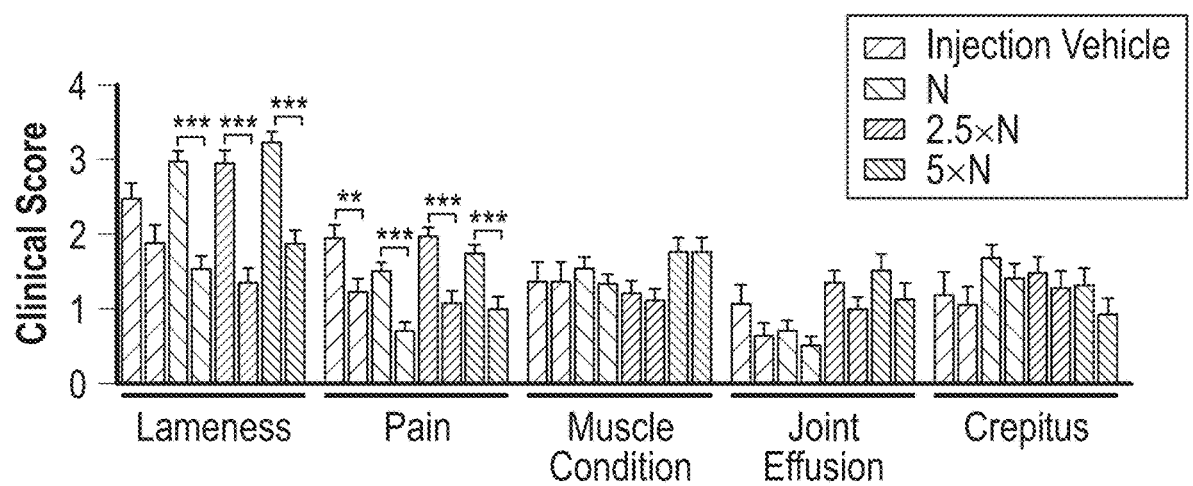
FIG. 8 is a series of bar charts showing data achieved in a canine model for day of treatment and one-year follow-up conducted with different doses of the inventive composition of the present invention.
Figure 9:
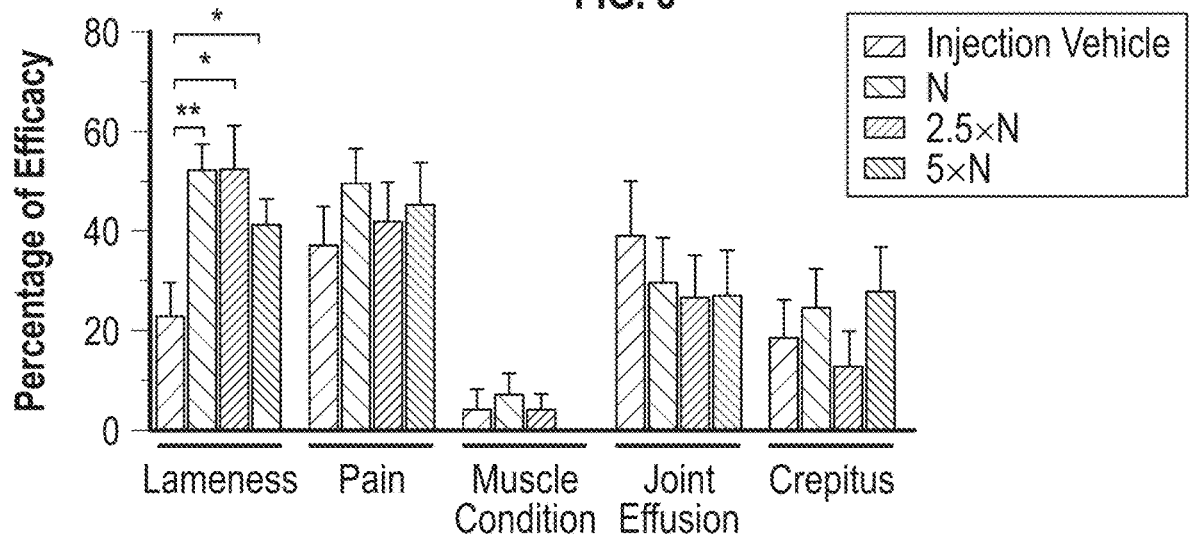
FIG. 9 is series of bar charts showing percentage efficacy of the treatments conducted as displayed in FIG. 8.
Figure 10:
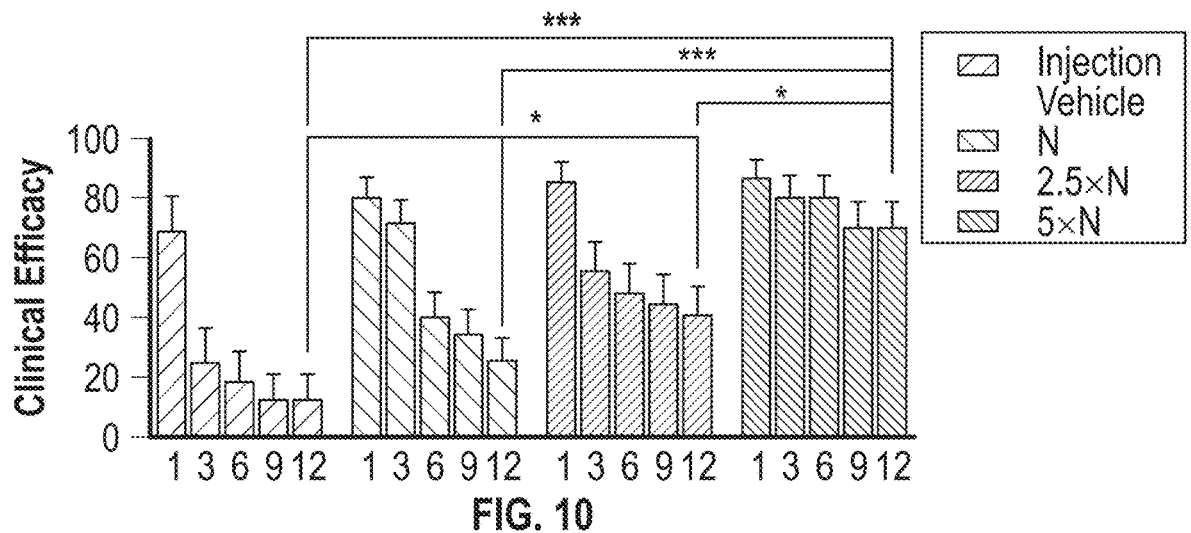
FIG. 10 is series of bar charts showing dose dependency and durability of the treatments conducted as displayed in FIG. 8 as a function of months from the treatment date.

Results of the study are discussed with respect to FIGS. 8-10. One month post-injection, lameness improved in all groups (FIG. 8), but not in the placebo group (23% reduction), with a reduction of 52%, 53% and 41% for the 2, 5 and 10 million cell groups, respectively (FIG. 9). All doses showed a significant benefit over the placebo at one month.

One month post-injection, pain improved in all groups by 37%, 49%, 41%, and 45% for the placebo, 2, 5, and 10 million cell groups, respectively (FIGS. 8 and 9). No statistical difference was observed relative to pain between the 2, 5 and 10 million cell groups. The placebo group showed transient efficacy, which may be explained by the fact that, before the cells were injected, the joint was washed with a saline solution to remove debris and thereby reduce inflammation. Efficacy was less than the efficacy obtained with the injection of gingival fibroblast cells.

For all other clinical parameters observed before the injection and one month post-injection, i.e., muscle condition, joint effusion and crepitus, no improvement was observed with any of the treatments (FIGS. 8 and 9). However, for all parameters, cell therapy was significantly effective before and after treatment for all the doses used; the gender of the animal did not affect the efficacy of the treatment. No adverse events were observed during the first 72 hours. At one month, the efficacy of all groups was not affected by the weight, age or initial lameness of the dog, and no correlation was observed between the initial clinical condition of the dog prior to the injection and its age or weight.

One year post-injection, clinical efficacy was assessed based on the CBPI questionnaire (completed by the dog owners) and interviews. The mean duration of efficacy was 2.6, 5.5, 6.3 and 9.1 months for the placebo, 2, 5 and 10 million cell groups, respectively. All cultured cell groups differed significantly from the placebo group, with the 10 million cell group showing significantly longer efficacy than the 2 and 5 million cell groups. The percentage of dogs for which efficacy was observed 12 months post-injection was 12.5%, 25%, 40%, and 70% for the placebo, 2, 5 and 10 million cell groups, respectively, as depicted in FIG. 10. All cell groups showed a significant difference at 12 months compared to the placebo group, and the 10 million cell group showed a significant difference at 12 months compared to the 2 and 5 million cell groups.

Arthroscopy was performed on one dog prior to and four months after injection. The dog had a non-smooth cartilage edge with loss of joint ultrastructure (i.e., no defined gap and presence of inflammatory cells mixed with chondrocytes). Four months post-injection, arthroscopic histology showed smooth cartilage with a normal cartilage ultrastructure (i.e., chondrocytes in a well-defined lacuna). This case confirms the clinical observations of cartilage repair after an intra-articular injection of cultured cells prepared according to the invention.

The canine dose-response study demonstrated that intra-articular injection of 2, 5 and 10 million cells is more effective than the placebo in treating dogs with osteoarthritis one month and 12 months after injection of the treatment. While the effects on lameness one month after the injection were similar for all three doses, at twelve months, the 5 and 10 million cell doses were statistically different from the placebo while the two million cell dose was not. It is hypothesized that more than 50% success observed at one year may be related to cartilage repair.

The variability of subjects in the study, which was conducted in a non-controlled environment, is similar to the variability of the human population, hence suggesting the transferability of the results of the preclinical study to humans. Notably, the study was performed on a cohort of very different dogs in terms of breed, genetic background, gender and weight/size. The sustained clinical efficacy in a non-homogeneous canine population over one year demonstrates the significant potential and robustness of inventive composition for the treatment of knee osteoarthritis.

Treatment of Equine Tendinopathy

The objective of the study was to evaluate the tolerance and efficacy of a local injection of gingival fibroblasts in the treatment of acute tendinopathy of the deep digital flexor tendon in ten sport horses, including mares and geldings, racehorses and eventing horses. The study was conducted as a single 2.5 mL intratendinous injection of 20 million cultured equine gingival fibroblast cells in a suitable medium. A clinical examination was conducted on just prior to injection, and 90 days later. Scoring for the clinical evaluation considered deformation, sensitivity, and heat, each on a scale of 1 to 3—with 3 being worst, and a dynamic review of lameness on a scale of 1 to 5, with 5 being worst. An ultrasound examination of the injured limb also was conducted to determine hypo-echogenicity, with 5 indicating high hypoechogenicity, indicating severe inflammation.

The single injection administered by syringe consisted of: 2.5 mL sodium hyaluronate 1% solution, 25 mg sodium chloride, disodium phosphate, monosodium phosphate, water, 20 million equine cultured gingival fibroblasts as described above, 200 μL of pure conditioned medium and paracrine secretion by gingival fibroblasts for 24 hours. The composition of 500 mL of pure conditioned medium was L-glutamine, 2400 mg/L sodium bicarbonate, a buffering agent (HEPES), sodium pyruvate, hypoxanthine, thymidine, trace elements, growth factors and 1.1 mg/L phenol red. Gingival fibroblasts in suspension, of heterologous origin, were obtained from gum biopsies of foals at birth from volunteer owners.

The results of the study are set forth in FIG. 11, along with a detailed legend explaining the scoring system. In particular, as depicted in FIG. 11, at three months, ultrasound evolution showed for five horses (EC1_2, EC1_4, EC1_5, EC1_8 and EC1_10) complete disappearance of the hypoechogenic lesion area that was initially observed by ultrasound prior to the injection. Four horses (EC1_1, EC1_3, EC1_7 and EC1_-9) showed the persistence of some hypoechoic foci; one horse (EC1_-6) showed the persistence of a clearly hypoechoic lesion. The favorable evolution observed by ultrasound of the tendon lesion at three months after the injection was durable when re-examined six months later.

Ultrasound and clinical evolution also was assessed after more than six months: six horses presented a recurrence of tendonitis between 7 and 11 months post-injection; two horses were culled for other pathological causes; one horse (eventing, EC1_-7) resumed normal activities. All controlled galloping horses presented recurrence of tendonitis at less than 12 months. The racehorse (EC1_-8) showed a favorable evolution of his tendinitis at 12 months, and participated in eight races post-recovery, winning three wins and placing four times. In addition, although the deformity noted prior to injection persisted at the 90 day evaluation, ultrasound examination showed significant lesion filling, none of the horses showed lameness and very few exhibited heat or tenderness.

This trial demonstrated good ability of the gingival fibroblast compositions cultivated in accordance with the principles of the present invention to resolve tendinopathy in horses.

Treatment of Equine Fetlock Arthropathy

The objective of this study was to evaluate the tolerance and efficacy of local injections of equine gingival fibroblasts, cultured in accordance with the principles of the present invention, in the treatment of fetlock arthropathy of competition horses. Ten horses participated in the trial. The fetlock refers to the joint where the cannon bone, the proximal sesamoid bones and the first phalanx meet.

The study was conducted as a single 2.5 mL intra-articular injection of 20 million culture gingival cells in a suitable medium, with examinations conducted on day 3, day 10 and day 90. The injections of the 20 million cultured cells were prepared as described above for the tendinopathy study. Inclusion criterion were a clinical examination to evaluate passive flexion, degree of lameness, articular deformity and tenderness. At day 3, day 10 and day 90, the horses were examined for passive flexion, degree of lameness, articular deformity and sensitivity. Favorable outcomes included resumption of activities, resumption of training and resumption of participation in competitions.

Figure 12:
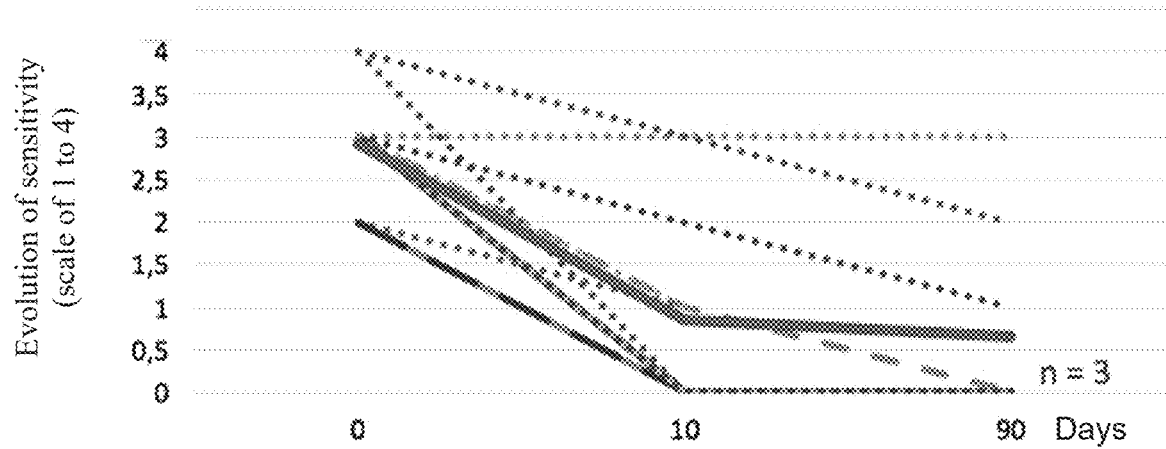
FIG. 12 is a graph showing summary results for sensitivity data obtained in a second equine group at ninety days after injections of a composition according to the present invention to treat tendinopathy.
Figure 13:
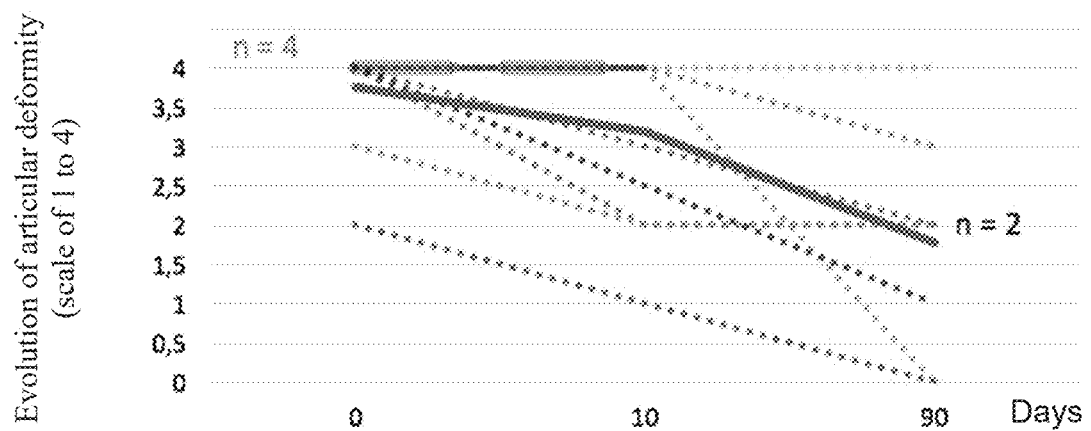
FIG. 13 is a graph showing summary results for articular deformation data observed in the second equine group at ninety days after injections of a composition according to the present invention to treat tendinopathy.
Figure 14:
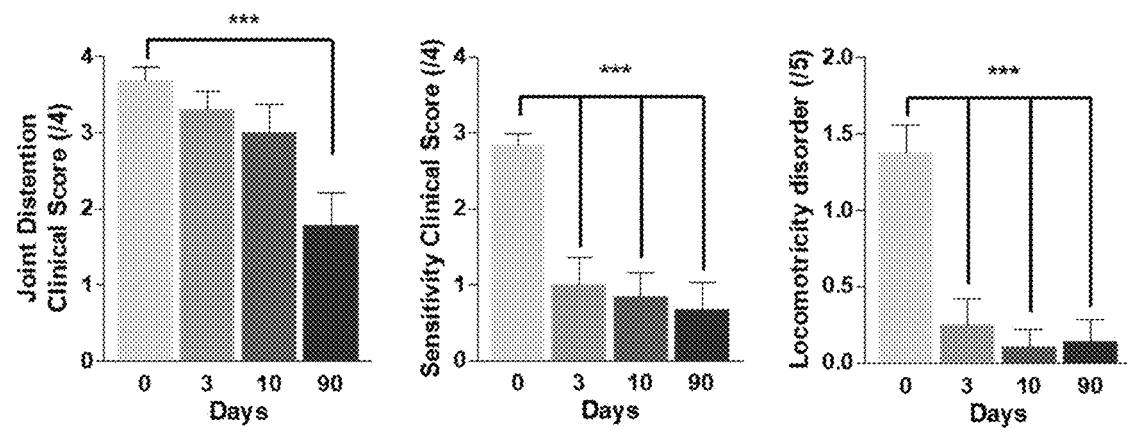
FIG. 14 is series of bar charts showing improvement in health scores in the second equine group as a function to days from the treatment date.

A group of ten horses of various ages and sexes participated in the study. The results of the study are set forth in FIGS. 12-14. As depicted in FIGS. 12 and 14, by Day 3, many horses experienced a 100% decrease in sensitivity by Day 10 that persisted to Day 90, while other horses showed continued improvement in sensitivity throughout the observation period. Similarly, as shown in FIGS. 13 and 14, some horses by Day 3 experienced a decrease in articular deformity that stabilized and persisted to Day 90, while others showed continued improvement throughout the observation period. The right-most chart in FIG. 14 shows that all of the horses experienced a significant reduction in locomotor discomfort between the first and last examination.

Overall, this study showed that a decrease in sensitivity from a mean value at Day 0 of 2.92 to a mean value at Day 90 of 0.67, wherein the decrease at Day 10 is 71% and improvement continues at Day 90, where it reaches 77%. On average, articular deformity at Day 0 was 3.77 and reduced to 1.78 at Day 90, demonstrating that articular deformity takes longer to show improvement. At Day 10, the improvement in articular deformity was 15%, while at Day 90 it had improved to 53%. Overall, this study demonstrated that cultured equine gingival fibroblast injections according to the invention have a beneficial effect on articular deformity and tenderness in a subject presenting fetlock arthropathy and was well tolerated by the animals.

While various illustrative embodiments of the invention are described above, it will be apparent to one skilled in the art that various changes and modifications may be made therein without departing from the invention.

What is claimed is:

1. A pharmaceutical or cosmetic composition produced by a process comprising the steps of:
   obtaining equine gingival fibroblast cells representative of a naturally occurring population of equine gingival fibroblast cells in equine gum tissue;
   culturing the equine gingival fibroblast cells through four passages in a culture medium comprising 20% Fetal Bovine Serum (FBS) and Basic Fibroblast Growth Factor (bFGF); and
   during a fifth passage of the process, omitting the 20% FBS from the culture medium and adding exogenous Interleukin 1 Beta (IL-1β) in a concentration from 0.1 ng/ml to 10 ng/ml, wherein by completion of the fifth passage the equine gingival fibroblast cells correspond to cell phenotypes cultivated so that at least about 90% of the cells of the cultivated population express CD90 and CD63 and about 20% or less of the cells of the cultivated population express CD146; and
   collecting the culture medium having a protein expression produced by the fifth passage for use as the pharmaceutical or cosmetic composition.

2. The composition of claim 1, wherein about 10% or less of the cells of the cultivated population express at least one mRNA selected from the group consisting of CD146, VCAM1, CD19, ITGAM, CD3D, CD4, FZD9, NGFR, NANOG, POU5F1, SOX2, KLF4, MYC, TNF, IL1A, IL1B, IL17A, IL23A, OSM, IFI27, IF144L, RSAD2, IFIT1, IFNA1 and IFNG mRNAs.

3. The composition of claim 1, wherein at least about 50% of the cells of the cultivated population express at least one mRNA selected from the group consisting of TIMP1, CD9, CD81, THY, ITGB1, FST, and COL1A2 mRNAs.

4. The composition of claim 1, wherein the gingival fibroblasts are allogeneic.

5. The composition of claim 1, wherein the gingival fibroblasts are autologous.

6. The composition of claim 1, further including at least one pharmaceutically acceptable carrier or excipient.

7. A pharmaceutical or cosmetic composition made by a process comprising the steps of:
obtaining equine gingival fibroblast cells representative of a naturally occurring population of equine gingival fibroblast cells in equine gum tissue;
culturing the equine gingival fibroblast cells through four passages in a culture medium including 20% Fetal Bovine Serum (FBS) and Basic Fibroblast Growth Factor (bFGF); and
during a fifth passage of the process, omitting the 20% FBS and adding exogenous Interleukin 1 Beta (IL-1β) in a concentration from 0.5 ng/ml to 2 ng/ml to the culture medium, wherein by completion of the fifth passage the equine gingival fibroblast cells correspond to cell phenotypes cultivated so that at least about 90% of the cells of the cultivated population express CD90 and CD63 and about 10% or less of the cells of the cultivated population express CD146; and
collecting the culture medium having a protein expression produced by the fifth passage for use as the pharmaceutical or cosmetic composition.

8. The composition of claim 7, wherein about 10% or less of the cells of the cultivated population express at least one mRNA selected from the group consisting of VCAM1, CD19, ITGAM, CD3D, CD4, FZD9, NGFR, NANOG, POU5F1, SOX2, KLF4, MYC, TNF, IL1A, IL1B, IL17A, IL23A, OSM, IFI27, IFI44L, RSAD2, IFIT1, IFNA1 and IFNG mRNAs.

9. The composition of claim 7, wherein at least about 50% of the cells of the cultivated population express at least one mRNA selected from the group consisting of TIMP1, CD9, CD81, THY, ITGB1, FST, and COL1A2 mRNAs.

10. The composition of claim 7, wherein the gingival fibroblasts are allogeneic.

11. The composition of claim 7, wherein the gingival fibroblasts are autologous.

12. The composition of claim 7, wherein the composition comprises at least one pharmaceutically acceptable carrier or excipient.

13. A pharmaceutical or cosmetic composition made by a process comprising the steps of:
obtaining equine gingival fibroblast cells representative of a naturally occurring population of equine gingival fibroblast cells in equine gum tissue;
culturing the equine gingival fibroblast cells through four passages in a culture medium comprising 20% Fetal Bovine Serum (FBS) and Basic Fibroblast Growth Factor (bFGF); and
during a fifth passage of the process, omitting the 20% FBS from the culture medium and adding exogenous Interleukin 1 Beta (IL-1β) in a concentration from 0.1 ng/ml to 10 ng/ml, wherein by completion of the fifth passage the equine gingival fibroblast cells correspond to cell phenotypes cultivated so that at least about 90% of the cells of the cultivated population express CD90 and CD63 and about 20% or less of the cells of the cultivated population express CD146; and
collecting the culture medium having a protein expression produced by the fifth passage and adding at least one pharmaceutically acceptable carrier or excipient.

14. The composition of claim 13, wherein about 10% or less of the cells of the cultivated population express at least one mRNA selected from the group consisting of CD146, VCAM1, CD19, ITGAM, CD3D, CD4, FZD9, NGFR, NANOG, POU5F1, SOX2, KLF4, MYC, TNF, IL1A, IL1B, IL17A, IL23A, OSM, IFI27, IFI44L, RSAD2, IFIT1, IFNA1 and IFNG mRNAs.

15. The composition of claim 13, wherein at least about 50% of the cells of the cultivated population express at least one mRNA selected from the group consisting of TIMP1, CD9, CD81, THY, ITGB1, FST, and COL1A2 mRNAs.

16. The composition of claim 13, wherein the gingival fibroblasts are allogeneic or autologous.

17. The composition of claim 13, wherein the composition further comprises the cultured cell population of equine gingival fibroblast cells in which the cells are cultivated so that at least about 90% of the cells of the population express CD90 and CD63 and about 20% or less of the cells of the population express CD146.

* * * * *